(12) United States Patent
Alessi et al.

(10) Patent No.: US 10,508,984 B2
(45) Date of Patent: Dec. 17, 2019

(54) METHOD OF DETECTING THE IN-LIQUID STATE OF A MOBILE DEVICE, RELATED IN-LIQUID DETECTION SYSTEM, MOBILE DEVICE AND COMPUTER PROGRAM PRODUCT

(71) Applicant: STMicroelectronics S.r.l., Agrate Brianza (IT)

(72) Inventors: Enrico Rosario Alessi, Catania (IT); Giuseppe Spinella, Biancavilla (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 154 days.

(21) Appl. No.: 15/454,584

(22) Filed: Mar. 9, 2017

(65) Prior Publication Data

US 2018/0088024 A1 Mar. 29, 2018

(30) Foreign Application Priority Data

Sep. 27, 2016 (IT) .................. 102016000096685

(51) Int. Cl.
| | | |
|---|---|---|
| *G01N 19/10* | (2006.01) | |
| *G01N 21/27* | (2006.01) | |
| *H04N 9/083* | (2006.01) | |
| *H04N 9/73* | (2006.01) | |
| *G06F 1/16* | (2006.01) | |
| *H04M 1/18* | (2006.01) | |

(52) U.S. Cl.
CPC .............. *G01N 19/10* (2013.01); *G01N 21/27* (2013.01); *G06F 1/1626* (2013.01); *H04N 9/083* (2013.01); *H04N 9/735* (2013.01); *H04M 1/18* (2013.01)

(58) Field of Classification Search
CPC ........ G01N 27/06; G01N 19/10; G01N 21/27; G03B 17/08; G06F 13/24; G06F 13/385; G06F 13/4068; G06F 13/4282; G06F 2213/0042; G06F 2213/2424; G06F 1/1626; H04N 5/2257; H04N 5/23245; H04N 9/083; H04N 9/735; H04M 1/18

See application file for complete search history.

(56) References Cited

U.S. PATENT DOCUMENTS

| | | | |
|---|---|---|---|
| 2009/0201390 A1 | 8/2009 | Mimura et al. | |
| 2014/0377877 A1* | 12/2014 | Burgi | G01N 33/4972 436/120 |
| 2015/0179037 A1* | 6/2015 | Ren | G01L 7/18 340/522 |

FOREIGN PATENT DOCUMENTS

WO WO-2015113170 A1 8/2015

OTHER PUBLICATIONS

IT Search Report and Written Opinion for IT 201600096685 dated Apr. 26, 2017 (8 pages).

* cited by examiner

*Primary Examiner* — Pankaj Kumar
*Assistant Examiner* — Alazar Tilahun
(74) *Attorney, Agent, or Firm* — Crowe & Dunlevy (57) ABSTRACT

An in-liquid state of a mobile device is detected by processing color components indicative of an intensity of the ambient light at different wavelengths and a pressure data indicative of ambient pressure. A first plausibility index indicates a likelihood of an air/liquid transition as a function of variations of at least two color components. A second plausibility index indicates a likelihood of an air/liquid transition as a function of variations of said ambient pressure. If both the first and the second plausibility indices indicate a likely air/liquid transition event, an in-liquid state signal is generated.

27 Claims, 3 Drawing Sheets

METHOD OF DETECTING THE IN-LIQUID STATE OF A MOBILE DEVICE, RELATED IN-LIQUID DETECTION SYSTEM, MOBILE DEVICE AND COMPUTER PROGRAM PRODUCT

PRIORITY CLAIM

This application claims the priority benefit of Italian Application for Patent No. 102016000096685, filed on Sep. 27, 2016, the disclosure of which is hereby incorporated by reference in its entirety.

TECHNICAL FIELD

Embodiments of the present disclosure relate to techniques for determining whether a mobile device, such as a mobile phones or a wearable device, is immersed in a liquid, so called "in-liquid detection".

BACKGROUND

Nowadays, mobile devices, such as mobile phones or tablets, do not comprise merely communication modules, such as 2G/3G or 4G mobile transceivers and/or Wi-Fi transceivers, but comprise also a set of sensors such as:
  position sensors, including for example a Global Navigation Satellite System (GNSS) receiver, such as a Global Positioning System (GPS) receiver;
  one or more accelerometers, such as tri-axial accelerometers and/or gyroscopes;
  other environmental sensors, such as temperature, humidity, atmospheric pressure and/or magnetic sensors.

These sensing and communication modules have usually low-power, low latency and high accuracy and permit the development and use of location and context-aware services. For example, currently more than 1 million of applications, so called Apps, are available through the main application stores for mobile devices and the applications having location and context enabled features are growing in number.

Generally, the ability to discriminate the user's activity and/or user's location depends on the type of primitive information/sensor data provided by the various sensors of the mobile device. For example, the application installed on the mobile device may be configured to process the sensor data in order to determine the activities the user of the mobile device is performing, for example in order to determine whether the user is stationary, walking, fast walking, running, using a bicycle or vehicle, shopping, watching TV, sleeping, waking-up, etc. Generally, the application may monitor, elaborate and/or store the sensor data and/or propose some tasks.

This has even lead to the development of wearable mobile devices, such as smart-watches or fitness bracelets, which represent a subgroup of mobile device possibly not even including a mobile communication module, and which often include sensors adapted to monitor physical parameters of the user, such as the heartbeat, blood pressure, etc.

Currently, most mobile devices do not include in-liquid sensors, i.e. sensors for determining whether the mobile device is immersed in a liquid, such as water.

Generally, a mobile device may comprise so called Liquid Contact Indicators (LCI). These LCIs are primarily one-time chemical indicators, for example based on sticker papers, that change color when in contact with a liquid, such as water. Typically, these indicators are built with a manufacturer signature for avoiding reproduction and are often arranged in the headphone connector, the dock connector, near the SIM-card slot or underneath the battery cover, for example near the battery contacts. These LCIs are commonly found in most types of mobile devices, such as mobile phones, portable music players, laptop computers, and other types of electronics and are basically used to indicate that the mobile device has been immersed in water and the warranty should not be valid anymore.

However, such chemical indicators may not be used as in-liquid sensors, because the indicators are unable to determine whether the mobile device has been removed from the liquid. For example, the indicators may not be used to provide additional environmental information and/or information concerning the user's activity, such as swimming. Possible other applications for in-liquid sensors may include the automatic adaption of the camera white-balance algorithm within the mobile device when diving.

Moreover, chemical indicators are often controversial, because some consumers claim they are unreliable and used to deny warranty coverage for devices that have not suffered water damage but have merely been exposed for longer periods to a high humidity level.

There is accordingly a need in the art to provide improved solutions for detecting the in liquid state of a mobile device.

SUMMARY

According to one or more embodiments, a method of detecting the in-liquid state of a mobile device is presented. Embodiments moreover concern a related in-liquid detection system, mobile device and computer program product.

Various embodiments of the present disclosure relate to a detection system configured to detect the in-liquid state of a mobile device.

In various embodiments, the detection system comprises at least an optical sensor configured to generate a first signal comprising a plurality of color components being indicative of the intensity of the ambient light at different wavelengths, and a pressure sensor configured to generate a second signal being indicative of the ambient pressure.

In various embodiments, the detection system comprises moreover a processing system configured to generate an in-liquid state signal as a function of the first and the second signal.

For example, in various embodiments, the processing system receives the first signal and determines a first plausibility index indicating whether it is likely that the mobile device has performed an air/liquid transition as a function of the variations of at least two color components of the first sensor signal.

In various embodiments, the processing system receives also the second signal and determines a second plausibility index indicating whether it is likely that the mobile device has performed an air/liquid transition as a function of the variations of the second signal.

In various embodiments, the processing system may then determine the in-liquid state signal as a function of the first and the second plausibility indices. For example, in case both the first and the second plausibility indices indicate that it is likely that the mobile device has performed an air/liquid transition, the processing system may set the in-liquid state signal to a given value indicating that the mobile device has performed an air/liquid transition.

For example, in various embodiments, the first and the second plausibility indices indicate whether it is likely that the mobile device has been immersed in or removed from a liquid. Accordingly, in case both the first and the second plausibility indices indicate that it is likely that the mobile device has been immersed in the liquid, the processing system may set the in-liquid state signal to a first value indicating that the mobile device has been immersed in the liquid. Conversely, in case both the first and the second plausibility indices indicate that it is likely that the mobile device has been removed from the liquid, the processing system may set the in-liquid state signal to a second value indicating that the mobile device has been removed from the liquid.

In various embodiments, the processing system may determine the first plausibility index by comparing the variations of at least two color components of the first sensor signal with respective predetermined threshold values.

In addition or in alternative, the processing system may compare the variation of a lower frequency color component of the first sensor signal with the variation of a higher frequency color component of the first sensor signal. For example, in this case, the processing system may set the first plausibility index to a given value indicating that it is likely that the mobile device has performed an air/liquid transition when the lower frequency color component exhibits a stronger relative variation than the higher frequency color component. For example, in various embodiments, the processing system may evaluate these variations by calculating the ratio between the lower frequency color component and the higher frequency color component and comparing the variation of the ratio with a predetermined threshold value.

Similarly, the processing system may set the second plausibility index to a given value indicating that it is likely that the mobile device has performed an air/liquid transition when the second signal has a variation exceeding a given threshold.

Generally, the processing system may also receive one or more further signals from one or more further sensors and determine one or more further plausibility indices indicating whether it is likely that the mobile device has performed an air/liquid transition. In this case, the in-liquid state signal may also be determined as a function of these one or more further plausibility indices. For example, the further sensor(s) may be a position sensor, one or more accelerometers and/or a humidity sensor.

In various embodiments, the in-liquid state signal may be used to determine a user's activity, such as swimming. The in-liquid state signal may also be used to activate one or more gas or volatile organic compounds sensors and/or for performing a white balancing of a camera of the mobile device.

BRIEF DESCRIPTION OF THE DRAWINGS

Embodiments of the present disclosure will now be described with reference to the annexed drawings, which are provided purely by way of non-limiting example and in which.

DETAILED DESCRIPTION

In the following description, numerous specific details are given to provide a thorough understanding of embodiments. The embodiments can be practiced without one or several specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

Figure 1:
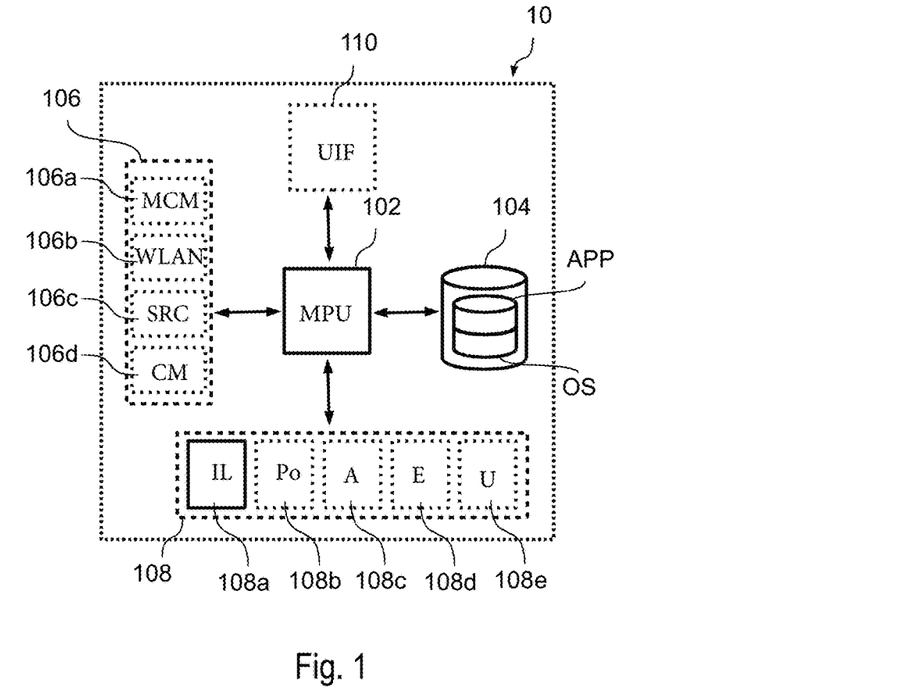
FIG. 1 shows an embodiment of a mobile device.

FIG. 1 shows an embodiment of a mobile device 10. Generally, the mobile device 10 comprises one or more processors (MPU) 102 connected to one or more memories 104. In various embodiments, the mobile device 10 comprises at least one of a communication interface 106 and/or a user interface (UIF) 110, such as a display and keyboard, or a touchscreen.

For example, the communication interface 106 may comprise at least one of:
 a mobile communication module (MCM) 106a, such as 2G, 3G and/or 4G mobile communication module, such as a GSM (Global System for Mobile Communications), GPRS (General Packet Radio Service), UMTS (Universal Mobile Telecommunications System), HSPA (High-Speed Packet Access), CDMA2000 and/or LTE (Long Term Evolution) transceiver;
 a WLAN (Wireless Local Area Network) transceiver 106b, such as a Wi-Fi transceiver in accordance with the IEEE 802.11 standard;
 a wireless short range communication (SRC) module 106c, such as a Bluetooth, Near Filed Communication (NFC) and/or Infrared transceiver; and/or
 a communication module (CM) 106d for communication via a cable, such as a USB (Universal Serial Bus) transceiver or an Ethernet communication module.

Those of skill in the art will appreciate that also other communication interfaces may be used, including those used for exchanging data with a memory card.

In various embodiments, the mobile device 10 comprises at least one sensor 108. Specifically, in various embodiment, the mobile device comprises at least one in-liquid (IL) sensor 108a. Generally, the mobile device 10 may comprise also other sensors, such as:
 a position (Po) sensor 108b, such as a Global Navigation Satellite System (GNSS) receiver, such as a Global Positioning System (GPS) receiver;
 one or more accelerometers (A) 108c, such as tri-axial accelerometers and/or gyroscopes;
 other environmental (E) sensors 108d, such as luminosity, temperature, humidity, atmospheric pressure and/or magnetic sensors.
 sensors (U) 108e adapted to monitor physical parameters of the user, such as the heartbeat, blood pressure, etc.

For example, typical mobile devices 10 are:
 a mobile phone comprising at least a mobile communication module 106a and a user interface 110,
 a smart watch comprising a communication interface 106, such as wireless short range communication module 106c, and a small touch screen 110, and a fitness bracelet possibly comprising one or more sensors 108e and either a communication interface 106, such as wireless short range communication module 106c, or a user interface.

Those of skill in the art will appreciate that the distinction between these categories of mobile devices 10 is nowadays becoming weak, because for example also smart-watches may comprise sensors 108e, thereby behaving as fitness bracelets.

In various embodiments, the memory 104 may contain an operating system OS, such as iOS®, Android® or Windows Mobile®, being executed by the processor 102 and which manages the general functions of the mobile device 10, such as the management of the user interface 110 and/or the communication via the interface(s) 106.

In various embodiments, the memory 104 may also contain one or more applications APP being executed by the operating system OS. For example, in various embodiment, the mobile device 10 comprises at least one application APP which, when executed by the processor 102, elaborates the sensor data provided by the sensor(s) 108. For example, a fitness application may acquire the sensor data from a position sensor 108b, an accelerometer 108c and the sensor(s) 108e in order to monitor the physical activity of the user. Conversely, a navigation application may acquire the sensor data from a position sensor 108b and possibly the accelerometers 108c in order to monitor the position and movement of the user.

Generally, the operating system OS may acquire the sensor data from the sensor(s) 108 in order to pre-elaborate the sensor data. The pre-elaboration may, for example, compute an absolute position information from the data provided by the position sensor 108b or determine inclination information of the mobile device 10 based on the data provided by the accelerometers 108c. Moreover, in various embodiments, the operating system OS may directly use the sensor data, for example in order to adapt the luminosity of the display 110 based on the data provided by a luminosity sensor 108d.

As mentioned in the foregoing, in various embodiments the mobile device 10 comprises an in-liquid sensor 108a.

Accordingly, in various embodiments, a waterproof mobile device 10, such as a wearable device, may comprise an application configured to monitor the user's activity, such as swimming, as a function of the in-liquid information provided by the sensor 108a. Conversely, the operating system OS of a mobile phone may be configured to use the in-liquid information, similar to a LCI, in order to set a flag that the mobile device 10 has been immersed in a liquid. Those of skill in the art will appreciate that the in-liquid information may also be used for other purposes, such as for human safety or indoor navigation applications.

Figure 2:
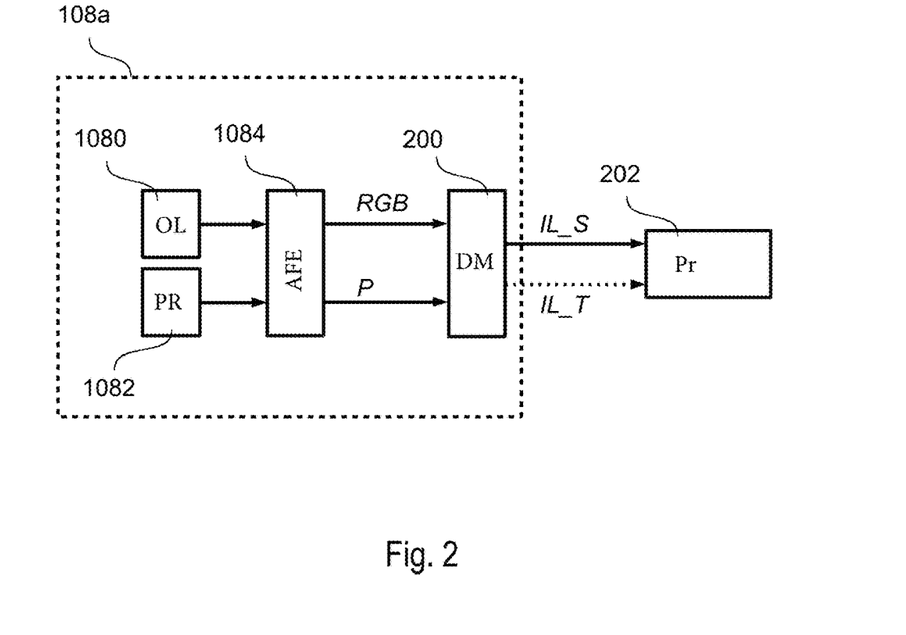
FIG. 2 shows a first embodiment of an in-liquid detection system using an optical sensor and a pressure sensor.

FIG. 2 shows a first embodiment of an in-liquid sensor 108a and respective detection system.

In the embodiment considered, the sensor 108a comprises two physical sensors 1080 and 1082.

In the embodiment considered, the first sensor is an optical light (OL) sensor 1080 configured to detect the intensity of the ambient light at two or more different wavelengths, i.e. for two different colors. For example, in various embodiments, the optical light sensor 1080 is a light sensor configured to detect the luminosity at least at three different wavelengths, such as a RGB (red-green-blue) color sensor. Accordingly, the sensor 1080 may be a modern ambient light sensor (ALS) providing RGB information. In various embodiments, the light sensor 1080 may also monitor the ultra-violet (UV) spectrum.

In various embodiments, the second sensor 1082 is a water resistant pressure (PR) sensor. Generally, the atmospheric pressure sensor 108d of the mobile device may be used for this purpose.

In the embodiment considered, the signals generated by the sensors 1080 and 1082 are fed to an analog front-end (AFE) 1084. For example, the analog front-end 1084 may amplify and/or filter the signals generated by the sensors 1080 and 1082, and/or perform an analog-to-digital conversion. Thus, generally, the analog front-end 1084 provides a first (analog or digital) sensor signal RGB being indicative for the intensity and color of the ambient light and a second (analog or digital) sensor signal P being indicative for the ambient pressure.

In the embodiment considered, the signals RGB and P are provided to the in-liquid detection module (DM) 200 configured to determine a signal IL_S being indicative of the in-liquid state of the mobile device 10 as a function of the signals RGB and P.

Generally, the module 200 may be any analog and/or digital hardware and/or software processing module. For example, in various embodiments, the module 200 may be a software module executed within the operating system OS or an application APP. Instead, for continuous in-liquid detection applications, an analog and/or digital low power hardware module is preferable.

Generally, the inventors have observed that an attenuation of the received light will occur when the mobile device 10 is immersed in water, i.e. when a transition occurs from air to water.

For this reason, in various embodiment, the module 200 determines the signal IL_S as a function of the variation of two or more of the spectral components detected by the optical sensor 1080, for example:

in the case where a negative gradient occurs in all spectral components, it is likely that the mobile device 10 has been immersed in a liquid, and in the case where a positive gradient occurs in all spectral components, it is likely that the mobile device 10 has been removed from the liquid, i.e. a transition from water to air occurs.

In various embodiment, the in-liquid detection module 200 may also generate an in-liquid trigger signal IL_T indicating that a state change of the signal IL_S occurred. For example, this trigger signal IL_S may be used by the operating system OS or an application APP in order to start some task.

Evidently, a similar attenuation of the signal RGB occurs when the ambient light conditions change rapidly. However, the inventors have observed that water behaves as a selective filter for light radiation, such as sunlight.

Figure 3:
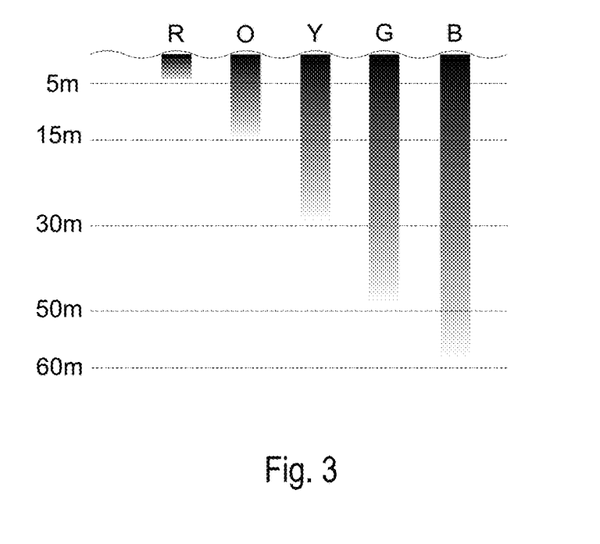
FIG. 3 schematically shows the optical attenuation behavior of water.

FIG. 3 shows in this regard schematically the absorption behavior of water for red R (650-780 nm), orange O (585-650 nm), yellow Y (575-585 nm), green G (490-575 nm) and blue B (380-490 nm) light. Specifically, the first wavelengths absorbed are the longer, less energetic wavelengths in the red region of the spectrum, while the blue and UV wavelengths penetrate the farthest into the water. For this reason, different colors are visible at various water depths and the deep water appears of a blue color. Evidently, many factors influence how light penetrates water, such as the amount of light available and light angle, the turbidity of the water, etc. However, still the various spectral components have different absorption characteristics.

Accordingly, in order to improve the reliability of the in-liquid detection, the module 200 may compare the variations of the various spectral components. For example, in various embodiment, the module 200 is configured for calculating one or more ratios between the various spectral components of the signal RGB and determined the signal IL_S as a function of the variations of these one or more ratios.

For example, in various embodiments, the in-liquid detection module 200 uses the ratio $R_{BR}$ between the blue B and the red R components, and:

in case a strong positive gradient occurs in the ratio $R_{BR}$ (i.e. the red component R has a sudden and stronger attenuation than the blue component B), it is likely that the mobile device 10 has been immersed in a liquid, and in case a strong negative gradient occurs in the ratio $R_{BR}$ (i.e. the stronger attenuation of the red component R is removed), it is likely that the mobile device 10 has been removed from the liquid.

For example, in pure water, the red/blue ratio may exhibit a change of about 20% in a water depth of 5-7 cm.

The inventors have observed that a similar change of the spectral components may also occur when the user enters a room with a particular illumination profile.

Accordingly, in various embodiments, the sensor data of the second sensor 1082 are used in order to reduce the risk of false detections.

Specifically, in various embodiments, the second sensor 1082 is a waterproof pressure sensor. Generally, an atmospheric pressure sensor is usually calibrated in order to sense the barometric pressure in the air. However, a fast change in the medium density (much higher in water than in air; for example at sea level the density of water is about 816 times greater than the density of air) will occur when an in-liquid transition occurs. An in-liquid transition will thus lead to a rapid variation in the sensed pressure signal P.

In various embodiments, the module 200 is thus configured to determine the in-liquid state signal IL_S also as a function of the variation of the pressure signal P.

Generally, also the variation of the pressure signal P is again only indicative for the in-liquid transition, because also other events may result in a sudden pressure change, such as entering a tunnel, etc. However, the inventors have observed that the combined use of an optical sensor 1080 and a pressure sensor 1082 significantly reduces the risk of false in-liquid detections. Moreover, such optical sensors 1080 and pressure sensor 1082 have a fast response compared to other types of sensors providing data being correlated with the in-liquid state of the mobile device 10, such as:

a humidity sensor, which has a rather slow response time;
two electrodes, which may detect the immersion immediately, but which are often unable to detect the exact moment when the mobile device 10 is removed from the liquid.

Moreover, the optical sensor 1080 and the pressure sensor 1082 have the advantage that such sensors are commonly used in mobile devices and thus no additional hardware components may be required and the complete processing could be implemented with software.

Figure 4:
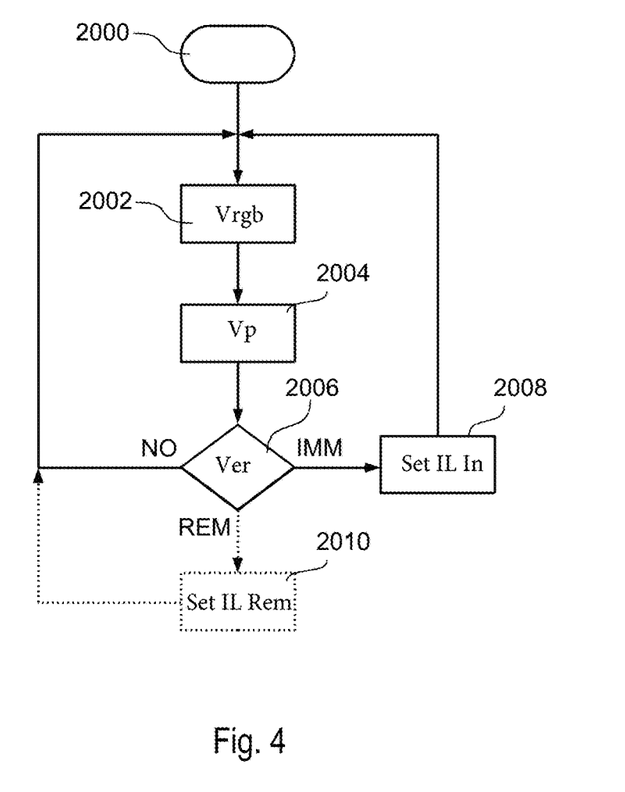
FIG. 4 shows an embodiment of a method of detecting the in-liquid state of a mobile device as a function of the data acquired from an optical sensor and a pressure sensor.

FIG. 4 shows in this respect a possible method for detecting the in-liquid state IL_S of the mobile device 10 as a function of the signals RGB and P.

After a start step 2000, the module 200 determines at a step 2002 the variations (Vrgb) of at least two color components of the sensor signal RGB, i.e. the variation of the light received by the sensor 1080 at least for two wavelengths, and calculates a first plausibility index indicating that it is likely that the mobile device 10 has been immersed in and/or removed from a liquid as a function of the variations of at least two color components of sensor signal RGB.

As mentioned in the foregoing, in various embodiments, the module may simply compare the variation of each of the at least two color components of sensor signal RGB with respective threshold values. In this case, the first plausibility index indicates that:

a) it is likely that the mobile device 10 has been immersed in a liquid when each of the at least two color components of the sensor signal RGB has a negative absolute or relative variation exceeding a respective given negative threshold; and b) it is likely that the mobile device 10 has been removed from the liquid when each of the at least two color components of the sensor signal RGB has a positive absolute or relative variation exceeding a respective given positive threshold.

In various embodiments, the thresholds are not fixed but the variations of at least two color components of sensor signal RGB are compared with each other.

For example, in alternative or in addition, the module 200 may determine at the step 2002 the absolute or relative variation of a higher frequency color component, for example the highest frequency color component (for example the blue component B), with respect to the absolute or relative variation of a lower frequency color component, for example the lowest frequency color component (for example the red component R), such as the ratio $R_{BR}$ between the blue B and the red R components. In this case, the first plausibility index may indicate that:

a) it is likely that the mobile device 10 has been immersed in a liquid when a positive variation of the ratio $R_{BR}$ exceeds a given positive threshold, i.e. the lower frequency color component exhibits a stronger relative decrease than the higher frequency color component; and b) it is likely that the mobile device 10 has been removed from the liquid when a negative variation of the ratio $R_{BR}$ exceeds a given negative threshold, i.e. the lower frequency color component exhibits a stronger relative increase than the higher frequency color component.

Evidently, the behavior has to be inverted when the ratio is inverted, for example when the ratio $R_{RB}$ between the red R and the blue B component is used.

Thus generally, the first plausibility index is determined by comparing the absolute and/or relative variations of at least two color components of sensor signal RGB with one or more fixed or dynamic threshold values, wherein the dynamic threshold of a given color component may be determined as a function of the value of another color component.

At a step 2004, the in-liquid detection module 200 determines a second plausibility index indicating that it is likely that the mobile device 10 has been immersed in and/or removed from a liquid as a function of the variations (Vp) of the pressure signal P.

For example, as mentioned in the foregoing, the module 200 may simply compare the absolute or relative variation of the signal P with given threshold values. In this case, the second plausibility index may indicate that:

a) it is likely that the mobile device 10 has been immersed in a liquid when the pressure signal P has a positive absolute or relative variation exceeding a respective given positive threshold; and b) it is likely that the mobile device 10 has been removed from the liquid when the pressure signal P has a negative absolute or relative variation exceeding a respective given negative threshold.

Generally, also more complex calculations may be performed in the steps 2002 and 2004 for determining the first and second plausibility indices as a function of the signals RGB and P. For example, reference can be made to PCT Publication WO 2015/113170 A1 (incorporated by reference), which discloses a solution for determining the immersion of a mobile device in a liquid as a function of a pressure signal and which is incorporated herein by reference for this purpose.

Generally, the steps 2002 and 2004 may also be exchanged, i.e. the module 200 may first determine the variation of the pressure signal P and then the variation of the signal RGB. Moreover, also further verification steps may be introduced, for example in order to determine always the variation of a first signal (for example the pressure signal P) and the variation of a second signal (for example the signal RGB) only when a variation of the first signal has been determined.

In a step 2006, the module 200 verifies (Ver) the first and second plausibility indices. Specifically, in various embodiment, the module 200 is configured for:

- in case both the first and the second plausibility indices indicate that it is likely that the mobile device 10 has been immersed in a liquid (output "IMM" of the verification step 2006), the module 200 proceeds to a step 2008, in which the in-liquid state signal IL_S is set to a given logic level indicating that the mobile device 10 has entered a liquid;
- in case both the first and the second plausibility indices indicate that it is likely that the mobile device 10 has been removed from the liquid (output "REM" of the verification step 2006), the module 200 proceeds to a step 2010, in which the in-liquid state signal IL_S is set to a given logic level indicating that the mobile device 10 has been removed from the liquid; and
- in all other case (output "NO" of the verification step 2006), the module 200 does not change the in-liquid state signal IL_S.

In all cases ("NO", "IMM", "REM") the module 200 proceeds to the step 2002 for performing a new detection cycle. Generally, a wait step may be introduced for monitoring the in-liquid state periodically, for example once every 20-500 ms, for example once every 200 ms.

In the previous embodiments, the module 200 is configured to determine both, the immersion in and the removal from the liquid. However, generally, the in-liquid detection module 200 may also only detect the immersion for example in order to implement a liquid contact sensor. In this case, the in-liquid state signal IL_S, once having been asserted, may be stored in a non-volatile memory.

As mentioned before, in various embodiments, the in-liquid detection module 200 may generate a trigger signal IL_T indicating that a state change of the signal IL_S occurred. For example, in various embodiments, this trigger signal IL_T is asserted in the steps 2008 and 2010, i.e. when the in liquid state signal IL_S changes.

In various embodiments, the module 200 may also only detect air/liquid transitions (i.e. transitions from air to liquid or from liquid to air), i.e. the steps 2008 and 2010 may be combined.

For example, in various embodiments, the module 200 may determine at the step 2002 a first plausibility index indicating that it is likely that the mobile device 10 has performed an air/liquid transition as a function of the variations of at least two color components of said first sensor signal (RGB). For example, the first plausibility index may indicate:

a) it is likely that the mobile device 10 has performed an air/liquid transition when the variation of the ratio $R_{BR}$ is greater than a given threshold; and b) it is likely that the mobile device 10 has not performed an air/liquid transition when the variation of the ratio $R_{BR}$ is smaller than the given threshold.

Similarly, the module 200 may determine at the step 2004 a second plausibility index indicating that it is likely that the mobile device 10 has performed an air/liquid transition as a function of the variations of the pressure signal P. For example, the second plausibility index may indicate that:

a) it is likely that the mobile device 10 has performed an air/liquid transition when the variation of the pressure signal P is greater than a given threshold; and b) it is likely that the mobile device 10 has not performed an air/liquid transition when the variation of the pressure signal P is smaller than a given threshold.

Accordingly, also in this case, the module 200 may verify the first and second plausibility indices at the step 2006. Specifically, in various embodiment, the module 200 is configured for:

- in case both the first and the second plausibility indices indicate that it is likely that the mobile device 10 has performed an air/liquid transition, the module 200 may proceed to the step 2008, in which the in-liquid state signal IL_S is set to a given logic level indicating that the mobile device 10 has performed an air/liquid transition; and
- in all other case (output "NO" of the verification step 2006), the module 200 does not change the in-liquid state signal IL_S or sets the in-liquid state signal IL_S to a given logic level indicating that the mobile device 10 has not performed an air/liquid transition.

Accordingly, in various embodiments, the in-liquid state signal IL_S may be set when a transition occurs. In this case, the in-liquid state signal IL_S may be reset once the signal IL_S has been read.

For example, the detection of the transitions may be sufficient for monitoring the user's swimming activity.

In various embodiments (see for example FIG. 2), the in-liquid state signal IL_S and possibly the in-liquid trigger signal IL_S are fed to a processing (Pr) module 202 configured, for example, to monitor, verify and/or elaborate the in-liquid state signal IL_S. Generally, the module 202 may be any analog and/or digital hardware and/or software processing module. For example, in various embodiments, the module 200 is a digital software module implemented within the operating system OS and/or an application APP.

For example, in various embodiments, the module 202 may be an application APP installed on the mobile device configured for determining the user's activity as a function of given pattern of the in-liquid state signal IL_S. In various embodiments, the module 202 may be a camera application configured to regulate the white balancing of the camera of the mobile device 10 as a function of in-liquid state signal IL_S.

Generally, the module 202 may also take into account the signal RGB, for example in order to estimate the attenuation of the various spectral components (for example for performing the automatic white balancing function of the camera), and/or the signal P, for example in order to estimate the water depth.

For example, in case the module 200 detects only the air/liquid transitions, the module 202 may take into account the signals RGB and/or P in order to evaluate in line with the previous description whether an air-to-liquid or liquid-to-air transition occurred. Generally, the module 202 may also determine an initial state. For example, the user can decide the initial state based on the application setting or the module 202 may determine the initial state automatically, for example as a function of the pressure signal P, because few centimeters of water cause a change in the measured pressure usually being out the possible pressure values on the earth surface.

Based on the initial state and the detected transitions, the module 202 may then decide if the next transition is towards air or liquid, and so on for the next transitions.

Figure 5:
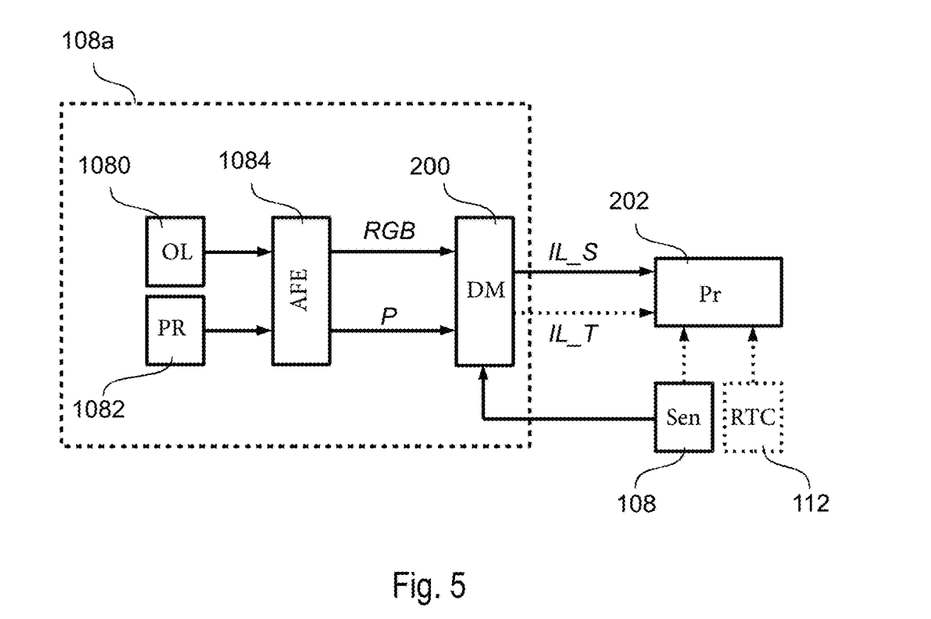
FIGS. 5 and 6 show further embodiments of in-liquid detection systems.

As shown in FIG. 5, the processing module 202 may also take into account sensor data provided by other sensors 108, for example in order to monitor the user's activity. Moreover, the module 202 may also acquire data from a real-time clock (RTC) 112, for example in order to log the user's activity.

Other possible applications may include an automatic activation of other sensors depending on the user context. For example, in various embodiments, the mobile device 10 may be configured to activate a gas and/or Volatile organic compounds (VOC) sensor(s) based on the in-liquid state signal IL_S, for example when the signal IL_S indicates a transition from water to air.

The embodiments described in the foregoing are thus based on the analysis of the attenuation of the chromatic components of the ambient light that depends of the wavelength/color of the light, because low frequency components have a stronger attenuation in water.

Evidently, the optical sensor 1080 will not provide meaningful data when there is no ambient light. Usually this is not a problem when monitoring the user's activity, because it is less likely that the user will, for example, perform swimming activity in this case.

Thus generally, as shown in FIG. 5, the in-liquid detection within the in-liquid detection module 200 may be improved by taking into account also sensor data provided by other sensors 108, such as a humidity sensor and/or an accelerometer. For example, reference can be made again to PCT Publication WO 2015/113170 A1 which discloses various embodiments for determining the in-liquid state without an optical sensor, and which is incorporated herein by reference for this purpose.

Figure 6:
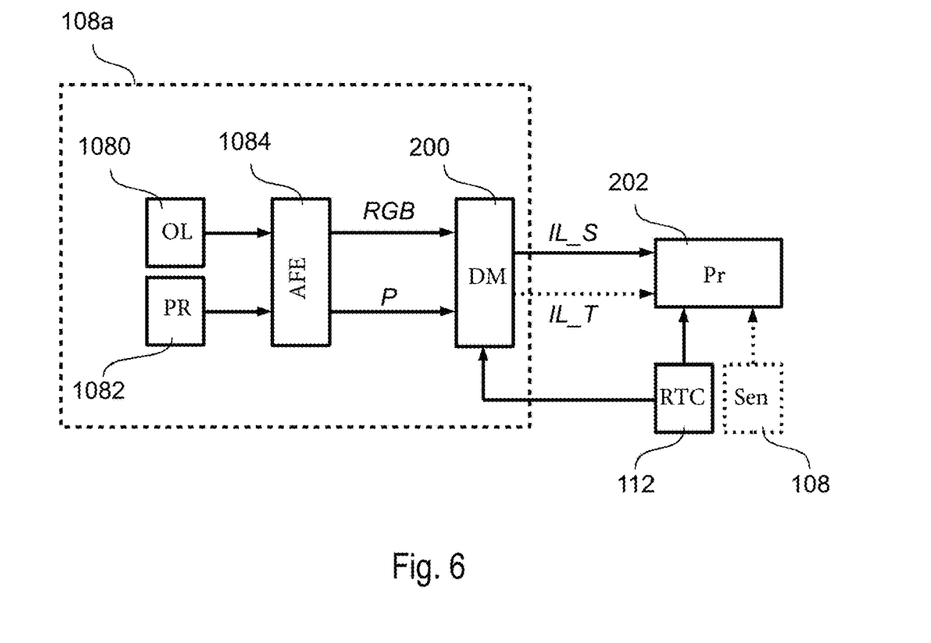

Similarly, as shown in FIG. 6, the in-liquid detection module 200 may also use the data from the real-time clock 112. For example, once having determined that the user is outdoor (for example based on the user's position as indicated by the sensor 100b), the module 200 may compensate the signal RGB in order to take into account the variation of the sunlight during a day.

Of course, without prejudice to the principle of the invention, the details of construction and the embodiments may vary widely with respect to what has been described and illustrated herein purely by way of example, without thereby departing from the scope of the present invention, as defined by the ensuing claims.

The invention claimed is:

1. A method of detecting an in-liquid state of a mobile device, comprising:
    receiving a first sensor signal comprising a plurality of color components indicative of an intensity of ambient light at different wavelengths;
    receiving a second sensor signal indicative of ambient pressure;
    determining a first plausibility index indicating a likelihood that the mobile device has performed an air/liquid transition as a function of variations of at least two color components of said first sensor signal;
    determining a second plausibility index indicating a likelihood that the mobile device has performed the air/liquid transition as a function of variations of said second sensor signal wherein determining the second plausibility index comprises:
        setting said second plausibility index to a given value indicating that it is likely that the mobile device has performed the air/liquid transition when said second sensor signal has a variation exceeding a given threshold; and
    generating an in-liquid state signal as a function of said first and said second plausibility indices, wherein in case both said first and said second plausibility indices indicate that it is likely that the mobile device has performed the air/liquid transition, said in-liquid state signal is set to a given value indicating that the mobile device has performed the air/liquid transition.

2. The method according to claim 1, wherein said first plausibility index indicates a likelihood that the mobile device has been immersed in or removed from liquid and said second plausibility index indicates a likelihood that the mobile device has been immersed in or removed from liquid, the method comprising at least one of:
    in case both said first and said second plausibility indices indicate a likelihood that the mobile device has been immersed in the liquid, setting said in-liquid state signal to a first value indicating that the mobile device has been immersed in the liquid; and
    in case both said first and said second plausibility indices indicate a likelihood that the mobile device has been removed from the liquid, setting said in-liquid state signal to a second value indicating that the mobile device has been removed from the liquid.

3. A method of detecting an in-liquid state of a mobile device, comprising:
    receiving a first sensor signal comprising a plurality of color components indicative of an intensity of ambient light at different wavelengths;
    receiving a second sensor signal indicative of ambient pressure;
    determining a first plausibility index indicating a likelihood that the mobile device has performed an air/liquid transition as a function of variations of at least two color components of said first sensor signal, wherein said determining the first plausibility index as a function of the variations of the at least two color components of said first sensor signal comprises at least one of:
        determining the first plausibility index by at least comparing the variations of the at least two color components of said first sensor signal with respective predetermined threshold values; and
        determining the first plausibility index by at least comparing the variation of a lower frequency color component of said first sensor signal with the variation of a higher frequency color component of said first sensor signal;
    determining a second plausibility index indicating a likelihood that the mobile device has performed an air/liquid transition as a function of variations of said second sensor signal; and generating an in-liquid state signal as a function of said first and said second plausibility indices, wherein in case both said first and said second plausibility indices indicate that it is likely that the mobile device has performed an air/liquid transition, said in-liquid state signal is set to a given value indicating that the mobile device has performed an air/liquid transition.

4. The method according to claim 3, wherein said comparing the variation of said lower frequency color component of said first sensor signal with the variation of said higher frequency color component of said first sensor signal comprises:
setting said first plausibility index to a given value indicating that it is likely that the mobile device has performed an air/liquid transition when the lower frequency color component exhibits a stronger relative variation than the higher frequency color component.

5. The method according to claim 3, wherein said comparing the variation of a lower frequency color component of said first sensor signal with the variation of a higher frequency color component of said first sensor signal comprises:
calculating a ratio between said lower frequency color component and said higher frequency color component of said first sensor signal; and
comparing a variation of said ratio with a predetermined threshold value.

6. The method according to claim 1, comprising:
receiving one or more third signals from one or more further sensors;
determining one or more third plausibility indices indicating a likelihood that the mobile device has performed an air/liquid transition as a function of variations of said one or more third signals; and
determining said in-liquid state signal also as a function of said one or more third plausibility indices.

7. The method according to claim 6, wherein said one or more further sensors comprise at least one of:
a position sensor;
one or more accelerometers; and
a humidity sensor.

8. The method according to claim 1, further comprising at least one of:
determining a user's activity at least as a function of said in-liquid state signal;
activating one or more gas or volatile organic compounds sensors as a function of said in-liquid state signal; and
performing a white balancing of a camera of said mobile device as a function of said in-liquid state signal, and said first sensor signal and/or second sensor signal.

9. A detection system for a mobile device, comprising:
an optical sensor configured to generate a first sensor signal comprising a plurality of color components indicative of an intensity of ambient light at different wavelengths;
a pressure sensor configured to generate a second sensor signal indicative of ambient pressure; and
a processing system configured to detect an in-liquid state of the mobile device by:
determining a first plausibility index indicating a likelihood that the mobile device has performed an air/liquid transition as a function of variations of at least two color components of said first sensor signal;
determining a second plausibility index indicating a likelihood that the mobile device has performed an air/liquid transition as a function of variations of said second sensor signal, wherein determining the second plausibility index indicating the likelihood that the mobile device has performed the air/liquid transition as a function of the variations of said second sensor signal comprises:
setting said second plausibility index to a given value indicating that it is likely that the mobile device has performed the air/liquid transition when said second sensor signal has a variation exceeding a given threshold; and
generating an in-liquid state signal as a function of said first and said second plausibility indices, wherein in case both said first and said second plausibility indices indicate that it is likely that the mobile device has performed an air/liquid transition, said in-liquid state signal is set to a given value indicating that the mobile device has performed an air/liquid transition.

10. The system of claim 9, wherein the mobile device is selected from a group consisting of a mobile phone, a smart watch and a fitness bracelet.

11. A method of detecting an in-liquid state of a mobile device, comprising:
detecting variation of at least two color components of an image;
determining from said detected variation of at least two color components of the image a first plausibility index having a value indicative of whether the mobile device has transitioned between an air environment and a liquid environment, wherein said determining the first plausibility index comprises:
comparing the variation of a first color component of the at least two color components to a first threshold,
comparing the variation of a second color component of the at least two color components to a second threshold, and
determining the first plausibility index based on results of said comparisons;
detecting variation of pressure;
determining from said detected variation of pressure a second plausibility index having a value indicative of whether the mobile device has transitioned between an air environment and a liquid environment; and
if both said first and said second plausibility indices have values that indicate that the mobile device has transitioned between an air environment and a liquid environment, then generating an in-liquid state signal for said mobile device.

12. The method of claim 11, wherein the in-liquid state signal for said mobile device has a first value indicating transition of the mobile device from the air environment to the liquid environment and has a second value indicating transition of the mobile device from the liquid environment to the air environment.

13. A The method of detecting an in-liquid state of a mobile device, comprising:
detecting variation of at least two color components of an image;
determining from said detected variation of at least two color components of the image a first plausibility index having a value indicative of whether the mobile device has transitioned between an air environment and a liquid environment, wherein said determining the first plausibility index comprises:
comparing a variation of a lower frequency color component of the at least two color components to a variation of a higher frequency color component of the at least two color components, and determining the first plausibility index based on a result of said comparison;
detecting variation of pressure;
determining from said detected variation of pressure a second plausibility index having a value indicative of whether the mobile device has transitioned between an air environment and a liquid environment; and
if both said first and said second plausibility indices have values that indicate that the mobile device has transitioned between an air environment and a liquid environment, then generating an in-liquid state signal for said mobile device.

14. The method of claim 13, wherein determining the first plausibility index based on a result of said comparison comprises setting said first plausibility index to a value indicating that it is likely that the mobile device has transitioned between an air environment and a liquid environment if the lower frequency color component exhibits a stronger relative variation than the higher frequency color component.

15. The method of claim 13, wherein comparing the variation comprises:
calculating a ratio between said lower frequency color component and said higher frequency color component of said first sensor signal; and
comparing said ratio to a predetermined threshold value.

16. A method of detecting an in-liquid state of a mobile device, comprising:
detecting variation of at least two color components of an image;
determining from said detected variation of at least two color components of the image a first plausibility index having a value indicative of whether the mobile device has transitioned between an air environment and a liquid environment;
detecting variation of pressure;
determining from said detected variation of pressure a second plausibility index having a value indicative of whether the mobile device has transitioned between an air environment and a liquid environment, wherein determining the second plausibility index comprises comparing said variation of pressure to a threshold and setting said second plausibility index to a given value if the threshold is exceeded; and
if both said first and said second plausibility indices have values that indicate that the mobile device has transitioned between an air environment and a liquid environment, then generating an in-liquid state signal for said mobile device.

17. The method according to claim 3, wherein said determining a second plausibility index indicating whether it is likely that the mobile device has performed an air/liquid transition as a function of the variations of said second sensor signal comprises:
setting said second plausibility index to a given value indicating that it is likely that the mobile device has performed an air/liquid transition when said second sensor signal has a variation exceeding a given threshold.

18. The method according to claim 3, comprising:
receiving one or more third signals from one or more further sensors;
determining one or more third plausibility indices indicating a likelihood that the mobile device has performed an air/liquid transition as a function of variations of said one or more third signals; and
determining said in-liquid state signal also as a function of said one or more third plausibility indices.

19. The method according to claim 18, wherein said one or more further sensors comprise at least one of:
a position sensor;
one or more accelerometers; and
a humidity sensor.

20. The method according to claim 3, further comprising at least one of:
determining a user's activity at least as a function of said in-liquid state signal;
activating one or more gas or volatile organic compounds sensors as a function of said in-liquid state signal; and
performing a white balancing of a camera of said mobile device as a function of said in-liquid state signal, and said first sensor signal and/or second sensor signal.

21. A detection system for a mobile device, comprising:
an optical sensor configured to generate a first sensor signal comprising a plurality of color components indicative of an intensity of ambient light at different wavelengths;
a pressure sensor configured to generate a second sensor signal indicative of ambient pressure; and
a processing system configured to detect an in-liquid state of the mobile device by:
determining a first plausibility index indicating a likelihood that the mobile device has performed an air/liquid transition as a function of variations of at least two color components of said first sensor signal, wherein said determining the first plausibility index as a function of the variations of the at least two color components of said first sensor signal comprises at least one of:
determining the first plausibility index by at least comparing the variations of at least two color components of said first sensor signal with respective predetermined threshold values; and
determining the first plausibility index by at least comparing the variation of a lower frequency color component of said first sensor signal with the variation of a higher frequency color component of said first sensor signal;
determining a second plausibility index indicating a likelihood that the mobile device has performed an air/liquid transition as a function of variations of said second sensor signal; and
generating an in-liquid state signal as a function of said first and said second plausibility indices, wherein in case both said first and said second plausibility indices indicate that it is likely that the mobile device has performed an air/liquid transition, said in-liquid state signal is set to a given value indicating that the mobile device has performed an air/liquid transition.

22. The system of claim 21, wherein the processing system compares the variation of said lower frequency color component of said first sensor signal with the variation of said higher frequency color component of said first sensor signal by setting said first plausibility index to a given value indicating that it is likely that the mobile device has performed an air/liquid transition when the lower frequency color component exhibits a stronger relative variation than the higher frequency color component.

23. A method of detecting an in-liquid state of a mobile device, comprising steps of:
detecting variation of at least two color components of an image;

determining from said detected variation of at least two color components of the image a first plausibility index having a value indicative of whether the mobile device has transitioned between an air environment and a liquid environment;

wherein said determining the first plausibility index from the detected variations of the at least two color components of the image comprises at least one of:
- determining the first plausibility index by at least comparing the variations of the at least two color components of the image with respective predetermined threshold values; and
- determining the first plausibility index by at least comparing variation of a lower frequency color component of the image with the variation of a higher frequency color component of said first sensor signal;

detecting variation of pressure;

determining from said detected variation of pressure a second plausibility index having a value indicative of whether the mobile device has transitioned between an air environment and a liquid environment; and if both said first and said second plausibility indices have values that indicate that the mobile device has transitioned between an air environment and a liquid environment, then generating an in-liquid state signal for said mobile device.

24. The method of claim 23, wherein the in-liquid state signal for said mobile device has a first value indicating transition of the mobile device from the air environment to the liquid environment and has a second value indicating transition of the mobile device from the liquid environment to the air environment.

25. The method of claim 23, wherein said determining the first plausibility index comprises comparing a variation of a first color component to a first threshold and comparing a variation of a second color component to a second threshold and determining the first plausibility index based on results of said comparisons.

26. The method of claim 23, wherein said determining the first plausibility index comprises comparing a variation of a lower frequency color component to a variation of a higher frequency color component and determining the first plausibility index based on a result of said comparison.

27. The method of claim 26, wherein determining the first plausibility index based on a result of said comparison comprises setting said first plausibility index to a value indicating that it is likely that the mobile device has transitioned between an air environment and a liquid environment if the lower frequency color component exhibits a stronger relative variation than the higher frequency color component.

* * * * *